United States Patent [19]

Eder

[11] Patent Number: 5,095,214
[45] Date of Patent: Mar. 10, 1992

[54] OPTICAL HOLE SEEKING APPARATUS HAVING DUAL SPACED LASER SCANNERS

[75] Inventor: Johannes Eder, Munich, Fed. Rep. of Germany

[73] Assignee: Erwin Sick GmbH Optik-Elektronik, Waldkirch, Fed. Rep. of Germany

[21] Appl. No.: 272,195

[22] Filed: Nov. 16, 1988

[30] Foreign Application Priority Data

Nov. 20, 1987 [DE] Fed. Rep. of Germany ....... 3739436

[51] Int. Cl.$^5$ ............................................. G01N 21/88
[52] U.S. Cl. ..................... 250/563; 250/572; 356/431
[58] Field of Search ................ 250/563, 562, 572; 356/431, 430, 375

[56] References Cited

U.S. PATENT DOCUMENTS

| | | | |
|---|---|---|---|
| 2,864,277 | 12/1958 | Eichorn | 250/572 |
| 3,331,963 | 7/1967 | Lippke | 356/431 |
| 4,310,250 | 1/1982 | Sick et al. | 356/431 |
| 4,389,575 | 6/1983 | Cole | 356/430 |
| 4,728,800 | 3/1988 | Surka | 250/572 |
| 4,737,649 | 4/1988 | Naruse | 356/430 |

*Primary Examiner*—David C. Nelms
*Assistant Examiner*—Que T. Le
*Attorney, Agent, or Firm*—Townsend and Townsend

[57] ABSTRACT

An optical hole seeking apparatus for webs (17) advanced in their longitudinal direction has two laser scanning devices (12, 15) which are arranged spaced apart along the web with a respective light receiving arrangement (11, 14) operating in reflection being associated with each laser scanning device. The two light receiving arrangements (11, 14) are connected to an electronic processing circuit (18) in which the two received photoelectric signals detected at the same position of the web (17) are correlated and then investigated to see whether they are the same or not.

14 Claims, 2 Drawing Sheets

OPTICAL HOLE SEEKING APPARATUS HAVING DUAL SPACED LASER SCANNERS

The invention relates to an optical hole seeking apparatus for webs, i.e. band-like material, which are advanced in their longitudinal direction, the apparatus comprising a laser scanning device which directs a scanning beam onto the surface of the web, with the scanning beam scanning the web transverse to its longitudinal direction along a scanning line; and a linear photoelectric light receiving arrangement disposed parallel to the scanning line which receives light influenced by holes in the webs from the scanning line and transmits an electrical signal to an electronic evaluation circuit, with the electrical signal being evaluated by the electronic evaluation circuit to see whether a shape and size is present which is characteristic for holes in the web.

FIELD OF THE INVENTION

Surface inspection apparatus operating with laser scanning devices and linear light receiving devices for the recognition of dark spots of all kinds and in all sizes are known in various forms, see for example German Offenlegungsschrift 28 57 076, German Offenlegungsschrift 28 27 705.

Such optical surface inspection apparatus admittedly basically allow hole recognition, it is however problematic to distinguish certain types of flecks, spots, stains, flaws or other surfaces from holes.

For this reason use has primarily been made, for hole seeking purposes, of hole seeking devices which operate in transmission, see for example German Offenlegungsschrift 28 08 359, German Offenlegungsschrift 29 34 554. These devices admittedly permit reliable hole recognition since light only passes through the web to the light receiving arrangement when holes are present, however these known hole seeking devices require a light transmitting device on one side of the web and a light receiving arrangement on the opposite side of the web.

This makes hole inspection impossible at locations of the moving web when the latter is guided over a deflection roller. Hole seeking by optical means can therefore only take place either before or after the deflection rollers where the web however flutters, in particular at high speeds, so that an unreliable hole indication signal is to be expected.

A further problem is caused by the relatively unsharp light bead. If a hole seeking apparatus of this kind is installed in addition to a surface inspection device then constructional difficulties occur.

SUMMARY OF THE INVENTION

The object of the present invention is thus to provide an optical hole seeking apparatus with reliable hole recognition capability wherein optical hole seeking can also take place in regions where the advanced web passes over light impermeable deflection rollers.

In order to satisfy this objection the invention provides that the photoelectric light receiving arrangement is disposed on the same side as the laser scanning apparatus and receives light reflected from the scanning line; that a second laser scanning device is disposed at a defined spacing A in the direction of advance of the web from the first laser scanning device on the opposite side of the web and scans the other side of the web at the defined distance A with a scanning line parallel to the first; that a further linear photoelectric light receiving arrangement extends parallel to the second scanning line and receives light reflected from this second scanning line and transmits an electrical signal to the electronic processing circuit; that the electrical signals transmitted from the two photoelectric light receiving arrangements to the electronic processing circuit are brought into correlation by intermediate storage of the first received signals; and that a hole signal is transmitted when both light receiving arrangements give substantially the same signal at the same position of the web.

The basic concept underlying the present invention is thus to be seen in the fact that the moving web is scanned by two separate light scanning devices and photoelectric light receiving arrangements from both sides at positions which are spaced apart in the longitudinal direction, and in that the received signals obtained through these scanning processes are correlated with one another in such a way that the two received signals are electronically compared at each instant which were obtained by scanning of the same point of the web but at different times.

As flecks, spots, stains etc. do not generally coincide on both sides of the web as a result of the statistical distribution the received signals originating from flecks or other flaws or structures on opposite surfaces of the web are fundamentally different. Signals originating from holes in the web are however practically the same independently from the side of the web at which the hole was detected by the laser scanning device and the associated light receiving arrangement.

If, therefore, two similar or identical fault signals are recognised by the electronic correlation device at the same position of the web then it is generally a reliable indication of the presence of a hole.

In accordance with the invention the two laser scanning devices and the light receiving arrangements are of exactly the same construction and they are also arranged at the same spacing from and at the same angles to the surface of the web.

It is particularly advantageous when the web is guided at the location of the laser scanning devices and light receiving arrangements around deflecting rollers in the one or other direction respectively. In this manner the light reflected from the surfaces of the rollers can be used in a particularly advantageous and effective manner for the initiation of a hole signal. In this case the hole seeking also takes place at a location of the web where the latter is guided particularly steadily and flutter-free as a result of the guidance at the rollers.

The advantages of the invention reside in the fact that no transmission receiver need be added as a result of the inspection of both sides of the web. Inspection can take place directly at the rollers. Problems with the building of the apparatus into existing web handling lines or production lines are thus avoided. The retrofitting of existing web guiding systems is possible at favorable cost due to the ability to do away with a transmission receiver.

When retrofitting a hole seeking apparatus in accordance with the invention into existing plants with advanced webs the two laser scanning devices with the associated light receiving devices can be arranged at any desired deflection rollers that are already present where sufficient space happens to be available.

The spacing of the two devices in the direction of advance of the web can be taken into account in the electronic circuit through suitable correlation. It is thus only necessary to precisely measure this separation once after installation of the laser scanning devices and the light receiving devices, to specify this spacing and to feed it permanently into the electronic evaluation circuit.

Bumps and dents in the surface of the web do not disturb the hole seeking and hole measurement processes. Faults such as dents and bumps admittedly appear simultaneously on both sides of the web, they deliver however a fault picture signal which is so different from that for holes that it is possible to distinguish between holes and bumps and dents in the electronic circuit without problem.

BRIEF DESCRIPTION OF THE DRAWINGS

The invention will now be described in the following by way of example only and with reference to the drawings in which are shown.

DESCRIPTION OF THE PREFERRED EMBODIMENTS

Figure 1:
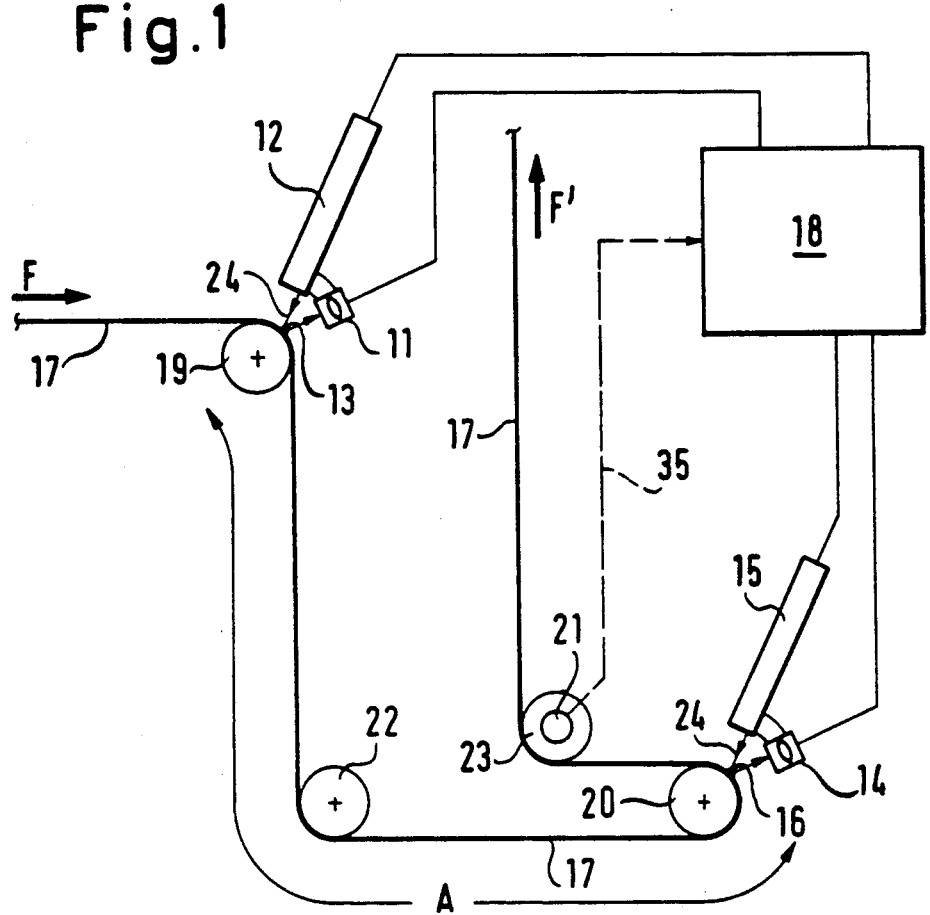
FIG. 1 a schematic sideview of an optical hole seeking apparatus in accordance with the invention when disposed at a moving web which is guided around one or more deflection rollers, FIG. 2 a plan view on the web in the region of the scanning line 13 or 16, and FIG. 3 a schematic representation of the two laser scanning devices used with the optical hole seeking apparatus of the invention and of the associated light receiving devices with the attached electronic evaluation circuit.

As seen in FIG. 1 a material web 17 which may possibly have holes at different positions is continuously advanced in the direction of the arrows F, F'.

The web 17 is first guided around a deflection roller 19 through approximately 90° and extends downwardly to a further deflection roller 22 which once again deflects the web 17 through 90° in the opposite direction. The web 17 then passes to a deflection roller 20 around which the web 17 is led through an angle of 180°. After this the web passes to a further deflection roller 23 which deflects the web through 90° in a vertical direction from where on it is guided upwardly out of the arrangement in the direction of the arrow F'.

Figure 2:
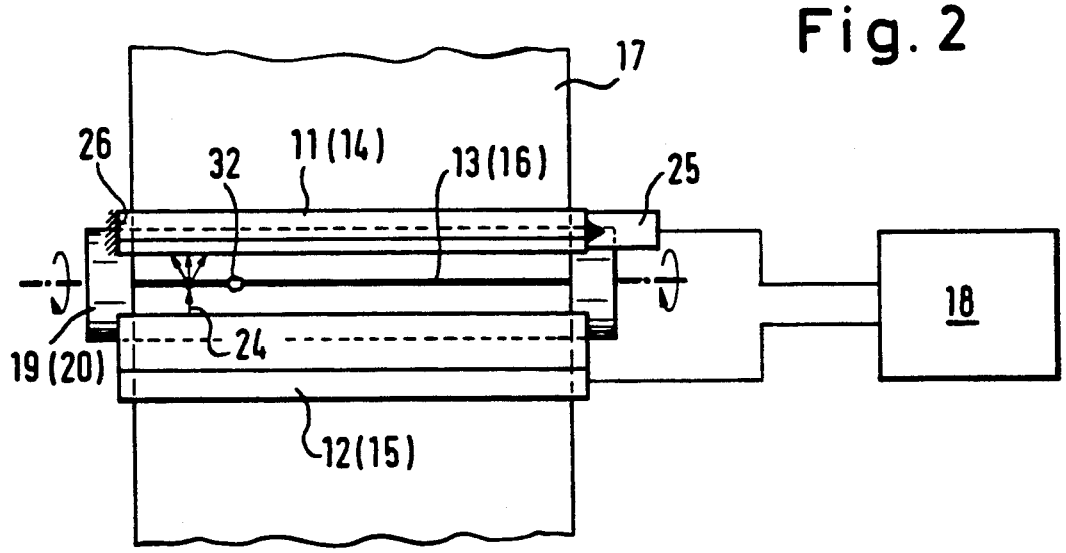
Figure 3:
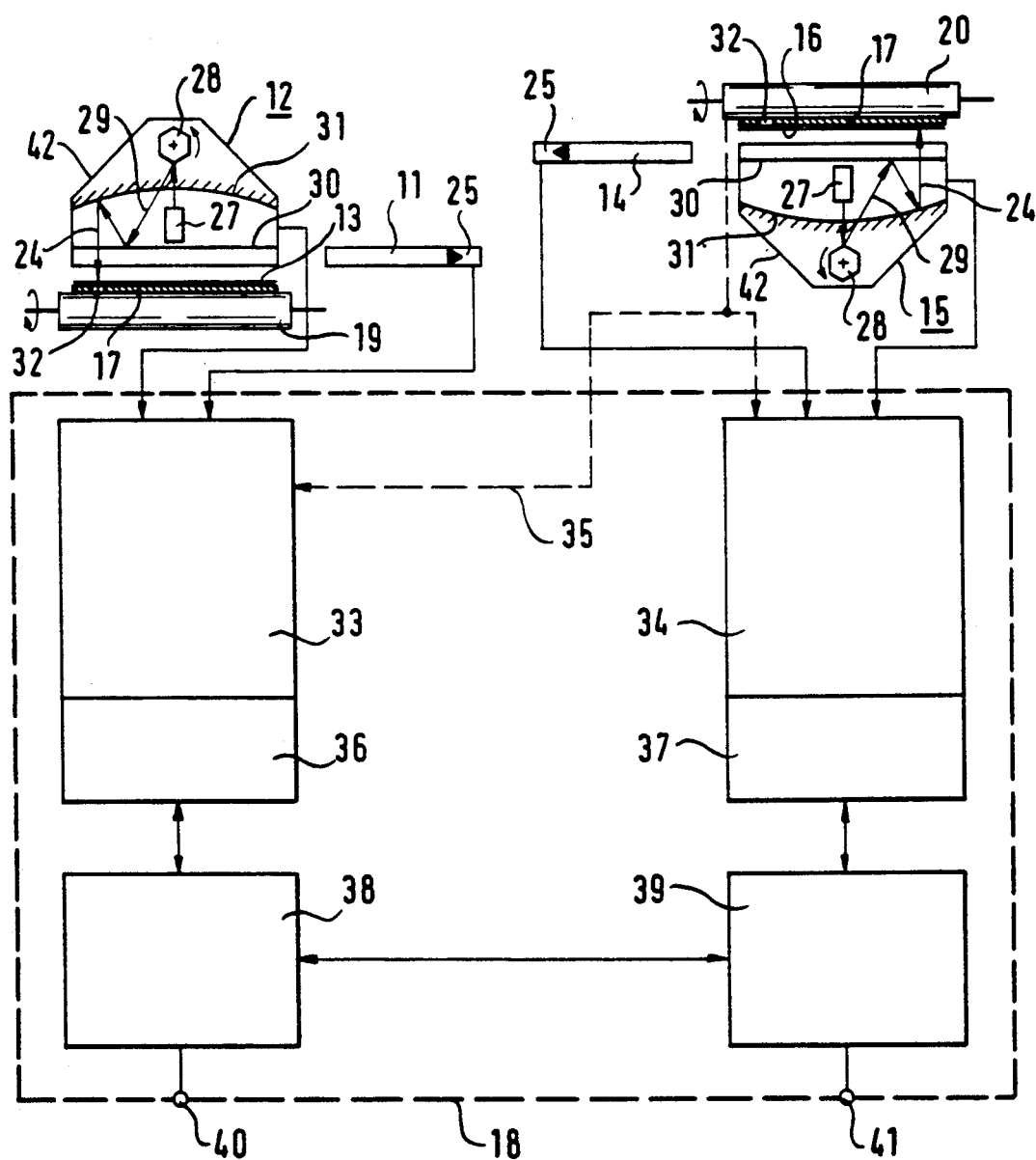

As seen in FIGS. 1 and 2 a laser scanning device 12 and a photoelectric light receiving arrangement 11 are arranged at the deflection roller 19. The laser scanning device 12 generates a scanning light bead on the web lying on the deflection roller 19 and the scanning light bead periodically scans the web along the scanning line 13, the direction from edge to edge which lies parallel to the axis of the deflection roller 19. The scanning beam 24 which emerges from the laser scanning device 12 and which is displaced parallel to itself in a plane perpendicular to the plane of the drawing impinges at an angle which deviates somewhat from the normal, but which is however relatively steep, onto the web 17 in the region of the scanning line 13, so that the light receiving arrangement 11 should be arranged at the angle of reflection relative to the surface of the web in order to receive as much light as possible which is reflected at the surface of the roller 19 in the event of the presence of a hole 32 (FIGS. 2, 3). Deflection rollers (19,20) can be selected to have a good contrast with the web (17). A relatively dark or mat deflection roller (19,20) may be selected with a shiny web, while a relatively shiny or bright deflection roller (19, 20) may be selected for a non-shiny web (17).

In corresponding manner an identically constructed second laser scanning device 15 is disposed above the deflection roller 20. Furthermore, a second photoelectric light receiving arrangement 14 which is constructed and mounted in corresponding manner to the light receiving arrangement 11 is located here at the angle of reflection.

The laser scanning devices 12, 15 and the light receiving arrangements 11, 14 are connected to an electronic evaluation circuit 18 to which an advance timing signal is also passed from an advance sensor 21 so that the electronic evaluation circuit 18 is informed at each instant in time over the degree of advance of the web 17.

The light receiving arrangements are formed in the embodiment of FIGS. 1 and 2 as light conducting rods 11 and 14 with a photomultiplier 25 being arranged at an endface of each of the light conducting rods, with the other endface being provided with a mirror coating 26 or being made reflecting in some other manner.

The construction of the laser scanning devices 12, 15 can be seen in schematical manner from FIG. 3. A laser 27 illuminates a mirror wheel 28, optionally via non-illustrated optical means, and the mirror wheel deflects a reflected scanning light beam 29 to a plane mirror 30 in strip form. The scanning light beam is reflected at this plane mirror 30 back to a strip-like concave mirror 31, with the reflecting surface of the mirror wheel 28 being located at the focal point of the strip-like concave mirror 31. The scanning beam 24 which is displaced parallel to itself is generated in this manner and emerges through a slot at the lower end of the housing of the laser scanning device 12 or 15 respectively, and there illuminates the surface of the web 17. In this way a laser light bead scans along the line 13. A hole in the web is shown by way of example at 32 in FIG. 3. While the laser scanning device 12 illuminates the web 17 from above the laser scanning device 15 is arranged beneath the web 17 and indeed at the distance A (FIG. 1) from the laser scanning device 12.

The light conducting rods 11 or 14 are shown specially displaced to the side in FIG. 3, simply for the purpose of better recognition relative to the laser scanning devices 12, 15. In actual fact the light conducting rods are arranged at the angle of reflection above and beneath the web 17 in accordance with FIGS. 1 and 2.

The distance A between the two scanning lines 13, 16 is shown in FIG. 1 by a line provided with arrows at the end. After installation of the apparatus this distance must be accurately measured and fed into the electronic processing circuit 18 so that the correct correlation is ensured.

In FIG. 3 the web 17 is shown at the right at a laser scanning device 15 at a later time point than at the laser scanning device 12. Between the two positions shown in FIG. 3 the web 17 has moved through the distance A (FIG. 1) from the scanning line 13 to the scanning line 16. It can be seen from FIG. 3 that the electronic processing circuit 18 has a signal processing stage 33, 34 following each of the light receiving arrangements 11 or 14 respectively. In accordance with the broken line 35, a signal representative of the advance of the web 17 is fed to each signal processing stage, in addition to a signal for the instantaneous position of the mirror wheel 28 and the received signal from the photomultipliers 25.

Threshold evaluation of the received signals and fault detection take place in the signal processing stages 33, 34. At the output of the signal processing stages 33, 34 interfaces 36, 37 are provided to two attached computers 38, 39 between which a computer interface, for example a parallel interface is located. Suitable output devices such as printers or monitors, are attached to the outputs 40, 41 of the computers 38, 39.

In the computers correlation takes place of the fault information which has been obtained and stored from the individual scans of the two laser scanning devices 12, 15 to form total fault signals. The fault information is investigated for possible holes, with it also being possible to specify the nature of the fault and the minimum hole size. Moreover, an exchange of possible hole error information takes place between the computers 38, 39. The hole information can be printed out with longitudinal and transverse coordinates. The holes which have been found are transmitted via the outputs 40, 41 to suitable output devices in the form of appropriate signals.

The length association in the electronic processing circuit 18 takes place in such a way that the individual scans of the laser scanning devices 12, 15 are synchronised hardware-wise to the web speed in order to be able to make a precise length statement (advance timing matching). For this purpose an advance timing generator is possible or a signal representative of the advance is derived from the web which is for example indicated by the broken lines 35 in FIGS. 1 and 3. It is important that the inspection systems for the upper side and lower side are connected into the same advance timing generator. Thus the same timing is always present from a dynamic viewpoint.

The length association can be very accurately realized on the basis of the measured length difference and the fact that an advance timing generator is used. A window can then be defined as a variable input parameter for the process in order to specify a search region.

The transverse association takes place in such a way that both laser scanning devices start scanning at the same edge of the web. For this one can use both a mechanical and an electronic synchronization of the two mirror wheels 28. The counting of the transverse coordinates starts at the edge of the web via an automatic edge recognition device effected in hardware. The transverse association can thus be directly effected.

A window can also be defined as a variable input parameter for the transverse coordinate in order to specify the search region.

In order to better define the reliable recognition of holes a width threshold and an amplitude threshold can be specified in the electronic evaluation circuit 18 for fault recognition.

The minimum hole size is an inputtable selectable parameter by which a specific minimum hole size can be specified.

The above named four criteria must be satisfied so that a hole can be recognized as such.

The minimum hole size to be found depends on the size of the laser light bead generated by the scanning beam 24 on the scanning line 13 or 16 and on the band (web) speed and the scanning frequency. The minimum hole size which can be recognized is approximately 1.5 times the light bead size.

I claim:

1. Optical hole seeking apparatus for webs which are advanced in their longitudinal direction, the apparatus comprising a first laser scanning device directing a scanning beam onto a surface of the web and scanning the beam along a first scanning line transversely to the longitudinal direction, a first linear photoelectric light receiving arrangement disposed on the same side of the web as the laser scanning device and parallel to the scanning line for receiving light reflected along the scanning line and transmitting an electrical signal, a second laser scanning device positioned at a defined spacing (A) in the direction of advance of the web from the first laser scanning device disposed on the opposite side of the web (17) and scanning the other surface of the web at the defined distance (A) along a second scanning line parallel to the first scanning line; a second linear photoelectric light receiving arrangement disposed on the same side of the web (17) as the second laser scanning device, extending parallel to the second scanning line, receiving light reflected along the second scanning line and transmitting a second electrical signal; an electronic processing circuit for evaluating the electrical signals to determine whether the signals are characteristic for holes in the web, the electronic processing circuit correlating the first and second electrical signals by intermediate storage of the first received electrical signal, the processing circuit transmitting a hole signal when the first and second light receiving arrangements give substantially the same signal characteristic for a hole in the web at the same position on the web.

2. Hole seeking apparatus in accordance with claim 1, including rotating deflection roller engaging and guiding the web at the location of the laser scanning devices and the light receiving arrangements in the one and other direction, respectively.

3. Hole seeking apparatus in accordance with claim 2, wherein the surfaces of the deflection rollers have a good contrast to the web, such as relatively dark or mat deflection rollers with a shiny web or relatively bright or shiny deflection rollers with a non-shiny web.

4. Hole seeking apparatus in accordance with claim 1, including an advance sensor for supplying an advance timing signal to the electronic evaluation circuit.

5. Hole seeking apparatus in accordance with claim 1, wherein the first and second photoelectric light receiving arrangements are light conducting rods with photomultipliers arranged at an end face thereof.

6. Hole seeking apparatus in accordance with claim 1, wherein the scanning beam plane of the laser scanning devices is scanned in a scanning beam plane which is disposed obliquely to the surface of the web in the region of the scanning lines; and in that the light receiving arrangements are arranged at the angle of reflection to the laser scanning devices.

7. Hole seeking apparatus in accordance with claim 1, wherein the scanning beams are scanned in scanning beam planes of the laser scanning devices which are disposed sufficiently steeply relative to the surface of the web in the region of the scanning lines so that light passing through the holes in the web to the surface of the rollers is reflected onto the light receiving arrangements.

8. Hole seeking apparatus in accordance with claim 1, wherein the laser scanning devices start each scanning cycle at the same edge of the web and the counting of the transverse coordinate starts at the relevant edge of the web by means of an automatic edge recognition device.

9. Hole seeking apparatus in accordance with claim 1, wherein for the transverse coordinate a window is defined as a variable input parameter in order to specify the search region.

10. Hole seeking apparatus in accordance with claim 1, wherein a threshold circuit is provided in the electronic evaluation circuit, the threshold circuit having a width threshold and an amplitude threshold, the width and amplitude thresholds each being capable of being specified for the fault recognition process.

11. Hole seeking apparatus in accordance with claim 1, wherein a selectable parameter for the minimum hole size can be fed into the electronic processing circuit by which a specific minimum hole size to be detected can be specified.

12. Hole seeking apparatus in accordance with claim 1, wherein an advance timing generator is used in order to realize the length association of the two laser scanning devices, with a window being defined as a variable input parameter in the electronic evaluation circuit in order to specify a search region.

13. Hole seeking apparatus in claim 1, wherein the first and second transverse scanning means includes a laser which directs a scanning beam onto a rotating mirror wheel having an axis of rotation perpendicular to the scanning line which when rotated causes transverse displacement of the reflected scanning beam, the scanning beam being reflected by the mirror wheel onto a plane mirror, the scanning beam being further reflected from the plane mirror to a concave mirror which has a focal point located at the mirror wheel, the scanning beam further being reflected by the concave mirror towards the web, the scanning beam impacting the web being substantially perpendicular to the scanning beam emitted from the laser.

14. Optical hole seeking apparatus for webs advancing in a longitudinal direction, the apparatus comprising first and second deflection roller engaging the web so that the webs travel along a portion of the periphery of the roller, a first laser scanning device having first transverse scanning means directing a scanning beam onto a first surface of the advancing web and scanning the beam along a first scanning line which extends across a portion of the web engaged by the first roller transversely to the longitudinal direction, whereby light passing through a hole in the web is reflected by the first deflection roller, a first light receiving arrangement disposed parallel to the first scanning line and positioned to receive light reflected along the first scanning line, the first light receiving arrangement generating a first electrical signal, responsive to light reflected along the first scanning line and indicating, as a first fault signal, when a hole is present at the first scanning line, a second laser scanning device disposed at a spacing (A) in the direction of advance of the web from the first laser scanning device on the opposite side of the web from the first scanning device, the second scanning device having second transverse scanning means directing a second scanning beam onto a second surface of the advancing web along a second scanning line which extends across the web and is parallel to the first scanning line, the second scanning line being located to scan across a portion of the web engaged by the second deflection roller so that light from the second scanning beam passing through a hole in the web is reflected by the second deflection roller, the second deflection roller rotating in an opposite direction to the first deflection roller, a second linear photoelectric light receiving arrangement arranged parallel to the second scanning line and receiving light reflected along the second scanning line, the second photoelectric light receiving arrangement generating a second electrical signal responsive to light reflected along the second scanning line and indicating, as a second default signal, when a hole is present along the first scanning line, an electronic processing circuit means receiving the electrical signals from the first and second light receiving arrangements and processing the signals to determine the presence of fault signals, the processing circuit means further bringing the first and second electrical signals into correlation by intermediate storage of the first electrical received signal and generating a hole signal when substantially the same first and second fault signals at the same position of the web are received.

* * * * *